United States Patent
Keller et al.

(10) Patent No.: US 12,128,364 B2
(45) Date of Patent: Oct. 29, 2024

(54) SPINNERET, DEVICE HAVING A SPINNERET, METHOD FOR PRODUCING A HOLLOW FIBER OR HOLLOW FIBER MEMBRANE BY MEANS OF A SPINNERET AND FILTER

(71) Applicant: FRESENIUS MEDICAL CARE DEUTSCHLAND GMBH, Bad Homburg (DE)

(72) Inventors: Torsten Keller, St. Wendel (DE); Jens Holger Stahl, Marpingen (DE); Eric Sommer, Poppenhausen (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 1174 days.

(21) Appl. No.: 16/611,219

(22) PCT Filed: May 9, 2018

(86) PCT No.: PCT/EP2018/062067
§ 371 (c)(1),
(2) Date: Nov. 6, 2019

(87) PCT Pub. No.: WO2018/206675
PCT Pub. Date: Nov. 15, 2018

(65) Prior Publication Data
US 2020/0156014 A1 May 21, 2020

(30) Foreign Application Priority Data
May 11, 2017 (DE) ...................... 10 2017 208 011.6

(51) Int. Cl.
*B01D 69/08* (2006.01)
*B01D 61/24* (2006.01)
(Continued)

(52) U.S. Cl.
CPC ......... *B01D 69/085* (2013.01); *B01D 61/243* (2013.01); *B01D 69/088* (2013.01);
(Continued)

(58) Field of Classification Search
None
See application file for complete search history.

(56) References Cited

U.S. PATENT DOCUMENTS

| 4,229,154 A | 10/1980 | Chaban, Jr. et al. |
| 5,551,588 A | 9/1996 | Hills |

(Continued)

FOREIGN PATENT DOCUMENTS

| CN | 1140769 A | 1/1997 |
| CN | 1821454 A | 8/2006 |

(Continued)

OTHER PUBLICATIONS

Office Action issued in corresponding Chinese Patent Application No. 201880031111.5 dated Aug. 16, 2021 (English translation only) (11 pages).

(Continued)

*Primary Examiner* — Jonathan M Peo
(74) *Attorney, Agent, or Firm* — Kilyk & Bowersox, P.L.L.C.

(57) ABSTRACT

A spinning nozzle is provided for the extrusion of a hollow fiber from one or more spinning masses. An apparatus that includes a spinning nozzle, and a method for extruding a hollow fiber using the spinning nozzle, are also provided. The spinning nozzle has an inlet port for each spinning mass to be extruded. The inlet port is for introducing the spinning mass into the spinning nozzle. An outlet port for the exit of a spinning mass along an outlet axis, is also provided. A spinning mass flow channel is used to guide the spinning mass from the inlet port to the outlet port. The spinning mass (Continued)

flow channel includes a flow manipulation section having an inlet and an outlet and includes a flow-guiding structure for influencing a spinning mass through the spinning mass flow channel.

24 Claims, 5 Drawing Sheets

(51) Int. Cl.
*D01D 4/06* (2006.01)
*D01D 5/24* (2006.01)

(52) U.S. Cl.
CPC ............. *D01D 4/06* (2013.01); *D01D 5/24* (2013.01); *B01D 2323/42* (2013.01)

(56) References Cited

U.S. PATENT DOCUMENTS

| | | | |
|---|---|---|---|
| 5,871,680 | A | 2/1999 | Macheras et al. |
| 6,454,943 | B1 | 9/2002 | Koenhen |
| 2004/0050791 | A1 | 3/2004 | Herczeg |
| 2005/0087637 | A1 | 4/2005 | Keller et al. |
| 2008/0268082 | A1* | 10/2008 | Keller .................. D01D 4/022 216/33 |
| 2013/0206062 | A1 | 8/2013 | Cobb et al. |
| 2013/0251909 | A1 | 9/2013 | Pedersen et al. |
| 2016/0279579 | A1* | 9/2016 | Fujiki .................. D01D 5/24 |
| 2017/0348644 | A1 | 12/2017 | Mizuta et al. |

FOREIGN PATENT DOCUMENTS

| | | |
|---|---|---|
| CN | 104203376 A | 12/2014 |
| CN | 104775171 A | 7/2015 |
| CN | 204589395 U | 8/2015 |
| DE | 3022313 A1 | 12/1980 |
| EP | 2112256 A1 | 10/2009 |
| EP | 2644757 A1 | 10/2013 |
| JP | 51-94806 U | 7/1976 |
| JP | 63105106 A | 5/1988 |
| JP | 2013000619 A | 1/2013 |
| KR | 910003164 A | 2/1991 |
| KR | 910009693 B1 | 11/1991 |
| WO | 0236327 A | 5/2002 |
| WO | 2017037912 A1 | 9/2017 |

OTHER PUBLICATIONS

Search Report issued in corresponding German Patent Application No. 10 2017 208 011.6 dated Jan. 2, 2018 (5 pages).
Office Action issued in corresponding Japanese Patent Application No. 2019-562364 mailed May 25, 2022 (English translation only) (3 pages).
International Search Report and Written Opinion issued in corresponding International Patent Application No. PCT/EP2018/062067 (with English translation of International Search Report) dated Sep. 3, 2018 (15 pages).
International Preliminary Report on Patentability issued in corresponding International Patent Application No. PCT/EP2018/062067 dated Nov. 12, 2019 (English translation) (9 pages).

* cited by examiner

SPINNERET, DEVICE HAVING A SPINNERET, METHOD FOR PRODUCING A HOLLOW FIBER OR HOLLOW FIBER MEMBRANE BY MEANS OF A SPINNERET AND FILTER

CROSS-REFERENCE TO RELATED APPLICATIONS

This application is a National Stage Application of PCT/EP2018/062067, filed May 9, 2018, published on Nov. 15, 2018, as International Patent Application Publication No. WO 2018/206675 A1, which claims priority to German Patent Application No. 10 2017 208 011.6, filed May 11, 2017.

DESCRIPTION

The present invention relates to a spinning nozzle for the extrusion of a hollow fiber from one or more spinning masses, in particular for the extrusion of a hollow fiber membrane from one or more spinning masses, wherein the spinning nozzle has an inlet port for each spinning mass to be extruded for introducing the spinning mass into the spinning nozzle, at least one outlet port for the exit of one or more spinning masses out of the spinning nozzle along an outlet axis, and at least one spinning mass flow channel for guiding at least one spinning mass to be extruded from the respective inlet port to the respective outlet port, whereby at least one spinning mass flow channel comprises a flow manipulation section having an inlet and an outlet, wherein the flow manipulation section exhibits a flow-guiding structure for influencing at least one spinning mass flowing through the spinning mass flow channel between the inlet and outlet of the flow manipulation section, whereby the flow-guiding structure of at least one flow manipulation section is thereby designed to influence the spinning mass flow such that at least a portion of the spinning mass flowing through the spinning mass flow channel flows through said spinning mass flow channel along at least two different flow paths.

The invention further relates to an apparatus for the extrusion of a plurality of hollow fibers or hollow fiber membranes from one or more spinning masses, wherein the apparatus comprises one spinning nozzle for each hollow fiber to be extruded.

The invention further relates to a method for the extrusion of a hollow fiber or a hollow fiber membrane from one or more spinning masses by means of a spinning nozzle.

The invention further relates to a filter, in particular a dialyzer, a plasma exchange filter or a membrane oxygenator for the extracorporeal treatment of blood.

Spinning nozzles for extruding fibers are used in particular in the production of chemical fibers, both in melt spinning as well as in dry spinning and wet spinning, and are known in principle from the prior art. Spinning nozzles generally have one or more round or angular plates, usually made of glass, metal or ceramic, with one or more shaping nozzle openings.

A spinning nozzle can shape a normally pressurized spinning mass into one or more finely spun strands, whereby chemical fibers are usually produced from polymer-based spinning masses.

In the extrusion process, viscose, curable masses are usually continuously pressed out of a form-giving opening, in particular a shaping nozzle opening, at a defined pressure, whereby bodies and/or profiles, also hollow bodies and/or hollow profiles, of any given length can in theory be produced with an opening of appropriate cross-sectional geometry.

By means of particularly immediate subsequent chemical and/or physical curing methods, for example by immediately bringing an extruded strand into contact with a precipitating agent, the extruded strand can be sufficiently cured into a filament which at least suffices for further processing, wherein curing methods can vary depending on the respective spinning method as well as the respective spinning mass utilized.

In most cases, nozzle opening cross sections are of circular disc-shaped form for hollow fibers, although it is also possible for hollow fibers to be produced with other profile cross sections. The cross section of the extruded filament is determined by the cross-sectional shape to the nozzle outlet ports. The flow rate, the opening cross section; i.e. the size of the nozzle opening's exit surface, as well as the strand draw-off speed thereby in particular influence the dimensions of the extruded strands and the filament produced therefrom.

A uniform spinning mass feed to the nozzle outlet port is a prerequisite for a filament of homogeneous properties, in particular homogeneous properties circumferentially as well as homogeneous properties over its length. Therefore, in addition to the cross-sectional shape of the nozzle opening and its dimensions, the spinning mass flow channels along which the individual spinning masses are fed to the nozzle outlet ports have a considerable impact on the performance characteristics and/or the working properties of the extruded filaments as they have significant influence on the spinning mass flow.

Hollow fibers are used in the textile industry as insulating material and/or as absorbent film material, whereby synthetic hollow textile fibers based on at least one polymer material are increasingly being used. In optics, hollow fibers can be used as conductors of light.

To produce hollow fiber membranes, which consist of at least two radial layers of which at least one layer is semipermeable, spinning nozzles able to be fed at least two different spinning masses are usually used, these usually being able to be fed in each case from physically separated spinning mass feed channels by a respective outlet port, whereby the individual outlet ports of the spinning nozzle are usually arranged concentrically to one another. In the process, nozzle outlet ports disposed further inwardly in the radial direction serve in the extrusion of a more inner layer of the hollow fiber membrane and the nozzle outlet ports disposed further outwardly serve in the extrusion of layers of the hollow fiber membrane disposed further outwardly.

Hollow fiber membranes are particularly suitable for the constructing of filter modules, whereby polymer-based hollow fiber membranes are usually produced via phase inversion in the wet-spinning process, wherein in particular the innermost and/or the outermost extruded spinning mass layer, which in each case usually comprises or consists of a polymer solution, is brought into contact with a precipitating agent while still in the spinning nozzle and/or brought into a precipitation bath with a precipitating agent after exiting out of the spinning nozzle so that a further processable filament results.

Spinning nozzles for the production of hollow fiber membranes are likewise known in principle from the prior art. For example, EP 2 644 757 A1 describes a generic spinning nozzle for extruding a hollow fiber membrane which discloses a spinning nozzle having multiple inlet ports for supplying a plurality of spinning masses on an upper side as well as an inlet port for supplying a precipitating agent and rotationally symmetric nozzle outlet ports arranged concentrically to an exit axis on an underside. The individual spinning masses are thereby each guided through separate, separately-formed spinning mass flow channels from a respectively associated separate inlet port to a respective outlet port until just before exiting out of the spinning nozzle, whereby one section of a respective spinning mass flow channel is configured to influence the spinning mass flow of the respective spinning mass to be extruded in order to achieve the most uniform possible spinning mass feed at the respective outlet port in each case. Each spinning mass to be extruded can thereby be provided with its own individual separate outlet port. However, two or more spinning masses can also be supplied to a shared outlet port.

A spinning nozzle for the extrusion of a multi-layer hollow fiber membrane is further known from WO 02/36327 A1, by means of which two, in particular different, spinning masses are brought into contact with each other while still inside the spinning nozzle such that a "wet-into-wet" spinning occurs, wherein an inner layer is extruded first and a second more outward layer then deposited atop the still wet first layer before exiting the spinning nozzle. This results in a close bonding of the first and second layer and thus in a multi-layer hollow fiber membrane less prone to delamination.

Further known from the prior art are hollow fiber capillary membranes used particularly in the medical field and in particular applicable to dialysis or in gas exchangers for extracorporeal membrane oxygenation (ECMO). In order to be able to provide the most compact dialyzers and/or gas exchangers possible along with a concurrently large exchange surface, such hollow fiber capillary membranes should in each case have the smallest possible diameter and wall thickness so that as many hollow fiber capillary membranes as possible can be accommodated in an available spatial volume and the largest possible exchange surface obtained.

The smaller the diameter and/or individual wall thicknesses and/or layer thicknesses of the individual membrane layers, the higher the requirements as to production accuracy, in particular dimensional accuracy, to the spinning nozzles necessary to produce such hollow fiber capillary membranes.

With that in mind, EP 2 112 256 A1 proposes applying a method of microstructure technology to produce a spinning nozzle for the extrusion of a hollow fiber capillary membrane and in particular utilizing a spinning nozzle having a plurality of plates structured by means of microstructure technology.

Apart from the high requirements on production accuracy and/or dimensional accuracy for a spinning nozzle for the extruding of hollow fiber capillary membranes, the uniform feed of the spinning mass to the outlet ports, in particular with decreasing layer thickness to the individual hollow fiber membrane layers, is further becoming increasingly important to hollow fiber capillary membranes in terms of achieving homogeneous membrane properties.

Although a variety of spinning nozzles designed in particular with respect to the most uniform possible spinning mass feed to the spinning nozzle outlet are known from the prior art, for example from WO 89/02938 A1 or CN 104775171 A, the desired homogeneity of the membrane properties usually cannot be achieved in the case of ultrafine hollow fiber capillary membranes having individual layer wall thicknesses of less than 100 Nm since the spinning mass is not supplied at sufficient uniformity.

In light of the above, one task of the invention is that of providing an improved spinning nozzle, by means of which in particular the homogeneity of an extruded hollow fiber can be improved, even in the case of hollow fibers having at least one layer with a wall thickness of less than 100 nm. A further task of the invention is that of providing a preferably stable spinning nozzle. It is moreover a task of the invention to provide an apparatus, in particular an apparatus of as constructionally simplest structure as possible, by means of which a plurality of improved hollow fibers can be produced simultaneously. It is moreover a task of the invention to provide a method by means of which a hollow fiber of particularly homogeneous properties can be produced, particularly also a hollow fiber with at least one layer having a wall thickness of less than 100 nm.

This task is solved by a spinning nozzle as claimed herein, by an apparatus as claimed herein, by a method as claimed herein, as well as by a dialyzer or a membrane oxygenator as claimed herein.

Preferential embodiments of the invention constitute the subject matter of the subclaims and the present description of the invention and will be explained in greater detail in the following. The wording of the claims is made a content component of the description.

In a spinning nozzle according to the invention, all of the at least two flow paths running through the spinning mass flow channel exhibit a substantially identical path length, in particular the same path length, at least between the inlet of the flow manipulation section and the associated outlet port of the spinning mass flow channel.

Because the path length between the inlet of the flow manipulation section and the associated outlet port of the spinning mass flow channel is the same for all of the at least two flow paths along which the spinning mass flows to the respective outlet port, a particularly uniform spinning mass feed can be achieved at the respective outlet port of the spinning mass flow channel, whereby a spinning mass flow which is in particular uniform over the circumference of the outlet port, preferably a substantially constant spinning mass flow, can be achieved. This enables a particularly homogeneous structure to the associated spinning mass layer of the hollow fiber and thus the production of a hollow fiber having particularly homogeneous properties.

When configured accordingly, particularly when the inventive spinning nozzle only has extremely low manufacturing tolerances, a spinning nozzle according to the invention enables the production of a hollow fiber of sufficiently homogeneous properties at individual wall thicknesses of less than 100 Nm, in particular in the range of 50 Nm, even when the spinning mass is fed to the spinning nozzle from one point, for example via a feed channel from above, which is advantageous from the manufacturing perspective.

A spinning nozzle according to the invention further enables in particular producing the finest hollow fiber capillaries or finest hollow fiber capillary membranes possible with particularly homogeneous properties.

A spinning nozzle in the sense of the invention is a nozzle which can be utilized in a spinning machine and by means of which the at least one filament; i.e. at least one individual fiber, can be produced, particularly a strand extruded.

A hollow fiber in the sense of the invention is a filament; i.e. an individual fiber having one or more continuous cavities in cross section.

A hollow fiber membrane in the sense of the invention is a hollow fiber consisting of at least one layer, whereby the at least one layer is a semipermeable layer. A hollow fiber membrane can consist of two or more layers, whereby the layers form the walls of the hollow fiber and act as a membrane.

A spinning mass in the sense of the invention is to be understood as the entire respective material mass fed to a spinning nozzle inlet port intended to at least partially form the at least one layer of the hollow fiber or hollow fiber membrane to be produced.

An outlet port in the sense of the invention refers to an opening from which at least one spinning mass and/or a reinforcing agent and/or a precipitating agent exits the spinning nozzle.

At least one outlet port of an inventive spinning nozzle is thereby preferably a gap, in particular a closed gap in the circumferential direction relative to an associated outlet axis, whereby at least one outlet port is preferably an annular gap, in particular a circular annular gap. The gap width of the outlet port can preferably be associated with a desired layer thickness of the hollow fiber for the spinning mass to be extruded through said outlet port.

An outlet axis in the sense of the invention refers to an axis which is parallel to a central exit direction of the associated spinning mass.

In an inventive spinning nozzle, preferably at least one outlet port is arranged con-centrically to the associated outlet axis and in particular rotationally symmetrical to same.

As defined by the invention, the inlet of a flow manipulation section is to be understood as an inlet port, in particular that inlet port via which a spinning mass enters into the flow manipulation section, whereby preferably each flow manipulation section comprises exactly one; i.e. just one single, inlet so that the inlet in each case defines a point of entry of the spinning mass into the flow manipulation section.

As defined by the invention, the outlet of a flow manipulation section is to be understood as an outlet port, in particular that outlet port via which a spinning mass exits the flow manipulation section, whereby preferably each flow manipulation section comprises exactly one; i.e. just one single, outlet so that the outlet in each case defines an exit point for the spinning mass out of the flow manipulation section.

A flow-guiding structure in the sense of the invention is a structure which is designed to guide and/or conduct a spinning mass flow in defined manner, in particular along a defined flow path.

For the construction of a spinning nozzle according to the invention, in particular for the construction and/or constructive design of at least one flow-guiding structure of an inventive spinning nozzle, it is befitting to draw on numeric methods, in particular numeric flow simulation (CFD-Simulation/Computational Fluid Dynamics) in conjunction with the application of one or several suitable optimization algorithms.

To that end, a presumptively suitable flow-guiding structure is preferably specified in parameterized form. Appropriate boundary conditions such as for example the position and geometry of the inlet and outlet of the flow manipulation section to be optimized and/or the associated outlet port and corresponding material parameters, in particular condition parameters of the respectively provided spinning mass, are furthermore indicated as boundary conditions so that the path lengths of the individual flow paths can in each case be determined with the assistance of the numerical flow simulation.

Depending on the embodiment of the flow-guiding structure, particularly the parameters defining the geometry of the flow-guiding structure are numerically determined by means of an optimization algorithm preferably following the geometry of said flow-guiding structure such that the same path length results for all the flow paths.

In one advantageous embodiment of a spinning nozzle according to the invention, at least one spinning mass flow channel of the spinning nozzle comprises a feeding section having a feeding section inlet and a feeding section outlet, wherein the feeding section inlet is preferably connected to at least one inlet port, in particular exactly one inlet port. The feeding section outlet is preferably connected to the inlet of at least one flow manipulation section, in particular an associated flow manipulation section, preferably exactly one associated flow manipulation section.

If the feeding section of a spinning mass flow channel is with only one inlet port and only one flow manipulation section and the respective flow manipulation section has only exactly one inlet, it is particularly simple to be able to achieve a defined entry of a spinning mass into the flow manipulation section; in particular the point of entry of the spinning mass can be precisely defined.

Correspondingly, a flow manipulation section having only one outlet enables a defined determining of the exit of a spinning mass from the associated flow manipulation section.

This can thereby significantly reduce the constructional complexity to a spinning nozzle according to the invention. In particular, the optimization problem to be solved can thereby be considerably simplified. As a result, the expenditure involved in constructing a spinning nozzle according to the invention is reduced. Above all, the time needed for calculating the construction of an inventive spinning nozzle relative to the spinning mass flow simulations and the required optimization operations can be significantly lowered.

The feeding section of a spinning mass flow channel can alternatively be connected to multiple inlet ports, whereby a plurality of spinning masses can easily be mixed together and, in particular, a spinning mass blend can be produced.

A spinning mass can furthermore be easily divided and in particular a multi-layer hollow fiber having a plurality of layers of the same spinning mass material easily produced when the feeding section of a spinning mass flow channel is alternatingly connected to multiple flow manipulation sections.

In one preferential embodiment of a spinning nozzle according to the invention, at least one flow manipulation section has a volume substantially limited by a floor surface, a ceiling surface and side surfaces, or is formed by a such volume, wherein preferably the floor surface and/or the ceiling surface of the flow manipulation section are formed by a flat surface, whereby in particular the floor surface and the ceiling surface are arranged parallel to one another, respectively extend parallel to each other.

In one preferential embodiment of a spinning nozzle according to the invention, at least one spinning mass flow channel comprises an outlet section having an outlet section inlet and an outlet section outlet, wherein the outlet section inlet is preferably connected to the outlet of at least one flow manipulation section, preferably an associated flow manipulation section, in particular exactly one associated flow manipulation section. Further preferably, the outlet section outlet is connected to an associated outlet port, in particular to exactly one outlet port, of the spinning mass flow channel.

Preferably, at least one outlet port of the spinning nozzle is of rotationally symmetrical design around the associated outlet axis, whereby the outlet port is of preferably fully circumferential configuration and in particular is an annular gap.

Preferably, at least one outlet section of at least one spinning mass flow channel is formed by a gap shaped as a circular cylindrical casing which is in particular arranged concentrically to the outlet axis and of rotationally symmetrical form to the outlet axis over its entire length.

In one preferential embodiment, a spinning nozzle according to the invention is designed for the extrusion of a multi-layer hollow fiber, in particular for the extrusion of a multi-layer hollow fiber membrane, particularly preferentially for the extrusion of a multi-layer hollow fiber capillary membrane having a diameter of less than 500 µm and a total wall thickness of less than 100 µm, wherein preferably each layer can be produced by the extrusion of a spinning mass, and wherein the spinning nozzle preferably comprises a separate inlet port for each spinning mass to be extruded for introducing the respective spinning mass into the spinning nozzle.

Thus, separate outlet ports can in each case be provided for each spinning mass, in particular for each spinning mass material, for the respective spinning masses to exit out of the spinning nozzle along an associated outlet axis, or else one or more outlet ports can also be provided for the exit of multiple spinning masses, in particular for the exit of different spinning mass materials.

When a spinning nozzle according to the invention has a separate individual outlet port for each spinning mass, in particular for each spinning mass material, a hollow fiber membrane of several layers can be extruded from the respective different spinning mass materials fed to the spinning nozzle, the layers of which are more or less separated from one another, whereby in particular a more or less pronounced separation between the individual spinning mass materials or spinning mass layers respectively can be achieved.

When, on the other hand, two or more spinning masses, in particular two or more differing spinning mass materials, can be output through a shared outlet port, there is usually at least partial mixing of the spinning masses, whereby layers with a less pronounced separation between the individual spinning masses/spinning mass materials can be produced.

Depending upon application, both separate outlet ports for each spinning mass as well as shared outlet ports for two or more spinning masses can be of advantage. With separate outlet ports, hollow fiber membranes with more defined, homogeneous properties to the individual hollow fiber membrane layers can usually be produced, particularly in a so-called dry merge, whereas shared outlet ports enable achieving, particularly in a so-called wet-into-wet merge, a better bonding of the individual spinning mass layers with one another, whereby the risk of delamination of the individual hollow fiber membrane layers can be reduced.

In one preferential embodiment, a spinning nozzle according to the invention preferably comprises a separate spinning mass flow channel for each spinning mass to be extruded to guide the spinning mass from the associated inlet port to the respective outlet port.

In a spinning nozzle having a plurality of outlet ports, all the outlet axes of the individual outlet ports preferably lie on a common nozzle outlet axis, whereby the individual outlet ports are in particular arranged concentrically to the common nozzle outlet axis; i.e. the outlet axes of the individual outlet ports preferably coincide. Preferably, the outlet ports are thereby designed and disposed, in particular the diameter and the gap width respectively selected, such that a multi-layer hollow fiber having the respectively desired layer thicknesses and/or wall thicknesses for the individual spinning mass layers is produced upon the exiting of the individual spinning masses out of the spinning nozzle.

Particularly preferentially, an inventive spinning nozzle has a separate inlet port, a separate spinning mass flow channel with a separate flow manipulation section as well as a separate outlet port for each spinning mass to be extruded, wherein preferably all of the outlet axes run parallel to one another and are in particular arranged along a common nozzle outlet axis; i.e. coincide. The radially innermost arranged spinning mass outlet port relative to the nozzle outlet axis thereby forms the outlet port for producing an innermost layer of the hollow fiber and the radially outermost arranged spinning mass outlet port forms the outlet port for extruding the outermost layer of the hollow fiber and the spinning mass outlet ports between them correspondingly form the outlet ports of the interposed spinning mass layers.

In an inventive spinning nozzle, the spinning mass flowing through the spinning mass flow channel flows at least partially along at least two different flow paths, in particular at least within the flow manipulation section. In other words, in an inventive spinning nozzle, a spinning mass flows at least partially along at least two different; i.e. varying, flow paths at least within a flow manipulation section. Particularly preferentially, the spinning mass flows through the spinning mass flow channel, in particular the respective flow manipulation section, at least partially along a plurality of different flow paths.

Particularly preferentially, all the flow paths of a spinning mass are not only of equal length, have the same path length respectively, from the inlet of the respective flow manipulation section to the associated outlet port but are moreover the same length from the inlet port of the respective spinning mass channel to the associated outlet port of the spinning mass flow channel and/or to a spinning center of the spinning nozzle.

The spinning center in the sense of the invention is to be understood as that point along a common nozzle outlet axis at which all the spinning masses coincide for the first time in the flow direction; i.e. at which the extruded hollow fiber first exhibits all the allotted spinning mass layers.

In one particularly advantageously embodiment of an inventive spinning nozzle, all of the at least two flow paths running at least partially through the spinning mass flow channel, preferably all the flow paths, exhibit a substantially identical path length between the inlet of the flow manipulation section and the outlet of the flow manipulation section.

This thereby enables further reducing the complexity of constructing a spinning nozzle according to the invention in a particularly simple manner, provided that the outlets of the respective flow manipulation sections with the respective outlet ports of connecting outlet sections of the respectively provided spinning mass flow channels are configured such that the respective spinning mass can flow through same uniformly, in particular likewise along flow paths of the same path length. In other words, this means that in an inventive spinning nozzle, preferably the outlet sections of the respectively provided spinning mass flow channels do not flow along different flow paths of different path lengths but in each case likewise along flow paths of the same path length.

In a further particularly advantageous embodiment of a spinning nozzle according to the invention, the spinning nozzle comprises at least one inlet port for introducing a reinforcing agent and/or a precipitating agent into the spinning nozzle, at least one outlet port for the reinforcing agent and/or precipitating agent to exit out of the spinning nozzle along an outlet axis, and at least one feed channel for conducting the reinforcing agent and/or precipitating agent from the respective inlet port to the associated outlet port, wherein the reinforcing agent and/or precipitating agent outlet port is preferably radially disposed and configured within the innermost spinning mass outlet port and in particular disposed and configured concentrically to said innermost spinning mass outlet port.

Termed a precipitating agent in the sense of the invention is thereby a liquid which is brought into contact with a spinning mass fed to the spinning nozzle for the extrusion of the hollow fiber, in particular with the spinning mass extruded as the innermost layer, in order to introduce a phase inversion and to at least partially cure the spinning mass extruded out of the spinning nozzle so as to enable a further processing of the extruded hollow fiber.

A reinforcing agent in the sense of the invention is a chemical agent or a chemical composition which serves in reinforcing the extruded hollow fiber, particularly a form-giving reinforcement. The reinforcing agent thereby serves to mechanically stabilize the extruded strand until it reaches a precipitation bath or the like for post-processing the extruded strands. The reinforcing agent can in particular also be a precipitating agent.

In some cases, it can be advantageous for at least one feed channel to be designed to conduct a reinforcing agent and/or a precipitating agent from the respective inlet port to the associated outlet port in the manner of a spinning mass flow channel and comprise at least one flow manipulation section and/or a feeding section and/or an outlet section, and in particular likewise designed to influence a reinforcing agent mass flow and/or a precipitating agent mass flow such that the reinforcing agent and/or precipitating agent flowing through the feed channel flow at least partially flows along two different flow paths, whereby all of the at least two flow paths running through the feed channel exhibit substantially the same path length between the inlet of the flow manipulation section of the feed channel and the associated outlet port of the feed channel, particularly the same path length between the respective inlet port and associated outlet port of the feed channel.

A spinning mass outlet port in the sense of the invention is thereby an outlet port provided for the exiting of a spinning mass, not for the exiting of a reinforcing agent and/or a precipitating agent.

In a further particularly advantageous embodiment of a spinning nozzle according to the invention, at least one flow manipulation section is arranged in a perpendicular orientation to the associated outlet axis, in particular normal to the associated outlet axis, relative to a central flow direction of a spinning mass flowing through the flow manipulation section. In other words, this means that at least one flow manipulation section is preferably arranged in a horizontal orientation, relative to a functional state of use of the spinning nozzle, whereby the associated outlet axis preferably runs vertically. This thereby enables achieving particularly simple construction of a spinning nozzle according to the invention and, as a result, economical production of an inventive spinning nozzle.

When the flow manipulation section is thereby formed by a volume which is limited by a floor surface, a ceiling surface and side surfaces, wherein the floor surface and/or the ceiling surface are in particular formed by flat surfaces, the floor surface and/or the ceiling surface are preferably oriented perpendicular, in particular normal, to the outlet axis.

When an inventive spinning nozzle comprises a plurality of flow manipulation sections, preferably at least two, in particular all, of the flow manipulation sections of the spinning nozzle are arranged parallel to each other.

When the outlet axes of all the outlet ports coincide and in particular lie on a common nozzle outlet axis, preferably at least one flow manipulation section is arranged in a normal orientation to the nozzle outlet axis, in particular all of the flow manipulation sections are arranged in a normal orientation to the nozzle outlet axis.

In a further advantageous embodiment of a spinning nozzle according to the invention, at least one inlet port is arranged on an upper side of the spinning nozzle with respect to a functional state of use of the spinning nozzle, whereby preferably all of the inlet ports are arranged on the upper side of the spinning nozzle.

Particularly preferentially, both all of the inlet ports provided for supplying a spinning mass as well as all of the inlet ports for supplying a reinforcing agent and/or a precipitating agent are thereby arranged on the upper side of the spinning nozzle. This enables multiple spinning nozzles to be arranged in space-saving manner in an apparatus, in particular a directly adjoining arrangement of multiple spinning nozzles, since no space needs to be kept free on the sides of the individual spinning nozzles for the spinning mass and/or reinforcing agent and/or precipitating agent feed. Thus, a particularly constructionally simple apparatus structure having multiple spinning nozzles can be provided to simultaneously produce multiple hollow fibers.

In this case; i.e. when at least one inlet port is arranged on the upper side of the spinning nozzle, preferably an associated feeding section of at least one spinning mass flow channel and/or feed channel for a reinforcing agent and/or a precipitating agent connected to the inlet port arranged on the upper side of the spinning nozzle runs in particular substantially parallel to the associated outlet axis and/or normal to the associated flow manipulation section, whereby a longitudinal axis of the feeding section is preferably arranged eccentrically; i.e. offset radially from the associated outlet axis and in particular runs beyond the outlet port.

By virtue of the equal-length flow paths of a spinning nozzle according to the invention, a uniform spinning mass feed to the outlet port can even be achieved with an eccentric and/or asymmetrical spinning mass feed relative to an associated outlet port and/or associated outlet axis and the lack of concentricity which acts to negatively impact the properties between a lumen of the hollow fiber and/or between the individual membrane layers of a hollow fiber membrane can be reduced or even completely eliminated.

In an alternative or additional, albeit in some cases likewise advantageous embodiment of an inventive spinning nozzle, at least one inlet port is arranged on a side of the spinning nozzle. All of the inlet ports can also be arranged on a side of the spinning nozzle. In this case, preferably an associated feeding section connected to the inlet port arranged on the side of the spinning nozzle runs substantially perpendicular to the associated outlet axis and/or parallel to the associated flow manipulation section, whereby a longitudinal axis of the feeding section is in particular arranged parallel to the associated flow manipulation section and in particular lies in a plane with the central direction of flow at which a spinning mass and/or precipitating agent and/or reinforcing agent flows through the respective flow manipulation section.

In both cases; i.e. when one or more inlet ports are arranged on an upper side of the spinning nozzle and/or laterally arranged, preferably at least one outlet port is arranged on an underside of the spinning nozzle, whereby in particular all the outlet ports are arranged on the underside of the spinning nozzle.

In a further advantageous embodiment of a spinning nozzle according to the invention, at least one inlet port and/or inlet of at least one flow manipulation section, in particular the inlet of an associated flow manipulation section, is arranged eccentrically to the associated outlet axis and in particular arranged radially beyond the outlet port relative to the outlet axis. Preferably all of the inlet ports for the spinning mass feed are thereby arranged eccentrically to the respectively associated outlet axis.

On the other hand, the inlet port for introducing a reinforcing agent and/or a precipitating agent can be arranged concentrically to the associated outlet axis. The concentric arrangement of the inlet port for the feed of reinforcing agent or precipitating agent is particularly appropriate when a flow manipulation section can be dispensed with and the desired properties of the hollow fiber to be extruded can be achieved with a feed channel extending concentrically from the inlet port to the outlet port.

However, if a reinforcing agent or precipitating agent flow through the spinning nozzle requires being respectively manipulated in order for a hollow fiber to be extruded with the desired properties, it is expedient for the inlet port for the reinforcing agent or precipitating agent feed to likewise be eccentrically arranged with a feeding section running parallel to the outlet axis, a flow manipulation section arranged in normal orientation to the outlet axis, and a feed channel running parallel to the outlet axis and in particular concentrically to said formed outlet section.

In a further advantageous embodiment of a spinning nozzle according to the invention, the outlet of at least one flow manipulation section is arranged concentrically to the associated outlet axis, wherein the outlet of at least one flow manipulation section is preferably of congruent design; i.e. congruent with the associated outlet port and arranged parallel to the respective outlet port particularly in the direction of the upper side of the spinning nozzle.

Preferably, the outlet of at least one flow manipulation section and/or at least one associated outlet port is designed rotationally symmetrical, whereby at least one outlet and/or at least one outlet port is in each case of preferably fully circumferential configuration and is in particular an annular gap.

If a flow manipulation section is thereby formed by a volume limited by a floor surface, a ceiling surface and side surfaces, the inlet of said flow manipulation section is preferably located in the ceiling surface and/or the outlet of the flow manipulation section in the floor surface.

In a further advantageous embodiment of a spinning nozzle according to the invention, the flow-guiding structure comprises at least one flow manipulation section of one or more flow guidance elements and/or one or more obstructing elements.

A flow guidance element in the sense of the invention is understood as an element which substantially serves in diverting and/or guiding and/or conducting a flow and which preferably comprises a flow guide surface having a flow-directing contour.

A flow guide surface thereby denotes a surface of the flow guidance element along which flows at least a portion of a spinning mass flow and by means of which the flow is diverted and/or guided and/or conducted, whereby the flow-directing contour; i.e. the geometry of the flow guide surfaces, in each case defines how the flow is diverted and/or guided and/or conducted.

As defined by the invention, an obstructing element is an element which substantially serves in changing the flow rate, whereby an obstructing element in the sense of the invention can thereby act both to increase flow rate as well as to decrease flow rate. With the appropriate configuration, an obstructing element can additionally effect an aligning of the flow.

Preferably, a spinning nozzle according to the invention comprises a plurality of successively arranged flow guidance elements in the direction of flow and/or one or more successively arranged obstructing elements in the direction of flow, whereby an inventive spinning nozzle particularly preferentially comprises a plurality of successively arranged flow guidance elements in the direction of flow and at least one obstructing element arranged downstream of the flow guidance elements in the direction of flow.

In a further advantageous embodiment of a spinning nozzle according to the invention, at least one flow guidance element is formed by a projection having a wall extending from a floor surface to a ceiling surface of the flow manipulation section, in particular by a projection having a wall of which at least part extends perpendicular to the floor surface and/or perpendicular to the ceiling surface of the flow manipulation section, whereby the wall at least partially forms a flow guide surface and has a defined flow-directing contour.

In a further advantageous embodiment of a spinning nozzle according to the invention, at least one flow guidance element is at least partly configured as a mass flow divider or forms a mass flow divider, whereby preferably at least one flow guidance element is designed as a mass flow divider dividing a spinning mass flow by a defined ratio or forms such a mass flow divider, in particular as a mass flow divider halving the spinning mass flow. A spinning mass flow can thus be easily divided into different flow paths, in particular at a defined ratio and in particular halved, whereby a uniform spinning mass flow can be achieved in a particularly simple way with the same path lengths to the individual flow paths.

In a further advantageous embodiment of a spinning nozzle according to the invention, at least one flow guidance element, in particular at least one mass flow divider, exhibits a flow-directing contour symmetrical to a first symmetrical plane, wherein the first symmetrical plane of the flow guidance element preferably extends perpendicular to the associated flow manipulation section, in particular parallel to the associated outlet axis.

In some cases, it is advantageous for at least one flow guidance element, in particular at least one mass flow divider, to be of overall symmetrical design; i.e. not only exhibit a symmetrically formed flow-directing contour but also the remaining contour of the flow guidance element which does primarily act as the flow-directing contour is of symmetrical design.

In a further advantageous embodiment of a spinning nozzle according to the invention, at least one flow guidance element, in particular at least one mass flow divider, exhibits a flow-directing contour similar to or as per a curly bracket; i.e. similar to the "curly bracket" punctuation mark or as per a flow-directing contour extending like a "curly bracket."

In some cases, it is advantageous for at least one flow guidance element, in particular at least one mass flow divider of a flow-directing contour, to extend in double-reflexed manner or like two symmetrically arranged integral signs connected longitudinally.

Preferably, a foremost leading edge and/or a foremost inflow area of the flow guidance element thereby lies in the first symmetrical plane.

Preferably, at least one flow guidance element, in particular at least one mass flow divider, is arranged in an orientation within the associated flow manipulation section such that the flow against the first symmetrical plane of the flow guidance element is from the front, particularly with a flow direction parallel to the first symmetrical plane.

The foremost inflow area is thereby understood in the sense of the invention as the part of the flow-directing contour of a flow guidance element, in particular that edge of a flow guidance element of initial inflow or, respectively, which a spinning mass flowing into a flow-directing contour encounters first when the spinning mass flows through the associated flow manipulation section.

In a further advantageous embodiment of a spinning nozzle according to the invention, the flow-guiding structure of at least one flow manipulation section exhibits a plurality of cascaded flow guidance elements, in particular a plurality of cascaded mass flow dividers, whereby the individual flow guidance elements are preferably arranged in a cascade formation having an odd number of stages, in particular in a three-stage cascade or in a five-stage cascade. When the flow guidance elements are thereby designed as halving mass flow dividers, a spinning mass flowing against same can thus be halved per mass flow divider in a first stage, quartered in a second stage and so on, in respect of a spinning mass flow entering into the flow manipulation section.

In a further advantageous embodiment of a spinning nozzle according to the invention, the flow-guiding structure of at least one flow manipulation section has only one flow guidance element, in particular only one mass flow divider, in a first stage of the cascade and two flow guidance elements, in particular two mass flow dividers, in a second stage of the cascade, whereby the flow guidance elements of the second stage of the cascade are preferably arranged at an approximate +/−90° offset orientation to the flow guidance element of the first stage of the cascade.

In the sense of the invention, arranged at an offset orientation by a defined angle thereby means an arrangement which is rotated by a defined angle.

In a further advantageous embodiment of a spinning nozzle according to the invention, $2^{(n-1)}$ flow guidance elements, particularly mass flow dividers in each case, are in each case provided in the nth stage for n>=2, which are preferably arranged offset by a respective $180°/2^{(n-1)}$ to the flow guidance elements of the (n−1)th stage, in particular symmetrically offset to same.

Thus, a spinning mass flow can be conducted along different flow paths, in particular along different flow paths of a defined path length, in particularly simple manner, wherein the respective path length can be lengthened by a defined amount by each further additional cascade stage. Depending on the arrangement of the individual flow guidance elements as well as their configuration, a respective flow path can thus be easily lengthened by a defined path length so that, as a result, the path length of at least two, preferably all of the flow paths of a spinning mass flow channel of an inventive spinning nozzle can be identically set.

In a further advantageous embodiment of a spinning nozzle according to the invention, a length of the flow-directing contour of at least one flow guidance element of the nth stage amounts to approximately ¼, or ¼ the length of the flow-directing contour of a flow guidance element of the (n−1)-th stage, whereby preferably one geometrical form of at least two flow guidance elements of adjacent cascaded stages is identical and/or self-similar. Preferably, this relationship respectively applies to all the flow guidance elements of a cascaded stage, in particular to all mass flow dividers of a cascade.

That is to say that a flow-directing contour of a mass flow divider of the second cascaded stage preferably amounts to ¼ the length of the flow-directing contour of a mass flow divider of the first cascaded stage.

In a further advantageous embodiment of a spinning nozzle according to the invention, at least one flow guidance element comprises a guide vane or is a guide vane, preferably a guide vane which at least partially conducts a spinning mass flow toward the outlet port, in particular a guide vane which at least partially conducts a spinning mass flow radially inwardly to the outlet port.

In other words, that is to say that a flow guidance element of an inventive spinning nozzle can be designed both solely as a guide vane or else as comprising one or more sections functioning as mass flow dividers and/or one or more guide vane sections.

In a further advantageous embodiment of a spinning nozzle according to the invention, the flow-guiding structure of at least one flow manipulation section comprises a plurality of guide vanes arranged concentrically to the outlet port and at an even circumferential distribution, the ends of which lying radially inward to the outlet of the flow manipulation section and/or to the associated outlet port are preferably arranged on a circular path of constant radius, whereby the guide vanes are in particular designed and disposed such that a respective spinning mass flow flowing along the guide vanes exits the guide vanes in a tangential direction relative to the outlet of the flow manipulation section and/or the associated outlet port.

Preferably, the ends of the guide vanes are thereby arranged concentrically to the outlet of the flow manipulation section, in particular concentrically to the outlet port.

A particularly uniform and in particular aligned spinning mass flow to the outlet of the flow manipulation section can be achieved with this type of guide vane arrangement and thus, with an appropriate configuration of the associated outlet section of the spinning mass flow channel, a particularly uniform spinning mass flow to the associated outlet port.

In a further advantageous embodiment of a spinning nozzle according to the invention, an inventive spinning nozzle comprises one or more guide vanes arranged on a far side of at least one flow guidance element of the highest cascaded stage from the flow-directing contour, whereby preferably at least one guide vane is of one-piece and/or integral design with a flow guidance element of the highest cascaded stage.

Preferably, all the guide vanes are thereby arranged on the far side of at least one flow guidance element from the flow-directing contour and are in particular in each case of one-piece and/or integral design with the respectively adjacent flow guidance element. A particularly advantageous flow-guiding structure thereby results when the respective flow guidance elements of the highest cascaded stage are thereby configured as mass flow dividers, in particular as respective halving mass flow dividers, each comprising a guide vane section on their far side from the flow-directing contour; i.e. on their rear side, which is in each case particularly of one-piece; i.e. integral configuration with a section of the flow guidance element forming the mass flow divider.

In other words, that is to say that the flow guidance elements of the highest cascaded stage are in particular flow guidance elements configured as mass flow dividers which preferably comprise a section formed as a guide vane on the far side from the flow-directing contour. Such flow guidance elements enable the advantageous providing of a particularly compact flow-guiding structure.

In some cases, however, it can be more advantageous to form one or more guide vanes separately from the flow guidance elements of the highest cascaded stage.

A flow-guiding structure of an inventive spinning nozzle can alternatively and/or additionally also comprise one or more flow guidance elements formed as mass flow dividers arranged in the downstream flow direction of one or more guide vanes or flow elements formed solely as guide vanes.

In a further advantageous embodiment of a spinning nozzle according to the invention, the flow-guiding structure of at least one flow manipulation section comprises at least one obstructing element which is formed by a wall extending from the floor surface to the ceiling surface of the flow manipulation section having a plurality of flow openings extending through the wall. Preferably, at least one obstructing element thereby comprises a wall extending perpendicular to the floor surface and/or to the ceiling surface having one or more flow openings of rectangular cross section and/or an arcuate progression through the wall.

One or more flow openings can also exhibit a circular cylindrical or oval cylindrical cross section or a tapering or expanding cross section which changes conically or flares out over the direction of flow or a cross-sectional geometry which differs therefrom. Particularly preferentially, all the flow openings are thereby arranged oriented to one another within the wall such that flowing through the flow openings results in an alignment of the spinning mass flow. This can be achieved for example by means of flow openings perpendicular to the wall or flow openings running in respective parallel arcs of identical curvature.

In a further advantageous embodiment of a spinning nozzle according to the invention, the flow-guiding structure of at least one flow manipulation section comprises an obstructing element formed by a circular cylindrical casing, which is preferably arranged concentrically to the outlet of the flow manipulation section and/or concentrically to the outlet port and/or concentrically to an associated outlet port and/or to an associated outlet axis.

Preferably, at least one flow manipulation section comprises an obstructing element which is formed by a vertical wall extending from the floor surface of the flow manipulation section to the ceiling surface of the flow manipulation section and a plurality of flow openings arranged within the wall and in a circumferentially even distributed arrangement and each of a cross-sectional width of approximately 5-20 μm, preferably approximately 10-15 μm. A dynamic pressure can thereby be increased upstream of the obstructing element and a homogenizing of the spinning mass flow and/or a reinforcing agent or precipitating agent flow achieved.

In particular, high shear rates of more than 500 l/s and even more than 1000 l/s can be achieved with such an obstructing element.

Preferably, at least one flow-guiding structure of at least one flow manipulation section thereby comprises an obstructing element radially arranged within the innermost flow guidance element, whereby preferably at least one flow-guiding structure comprises an obstructing element radially arranged within a cascade of flow guidance elements.

In a further advantageous embodiment of a spinning nozzle according to the invention, the flow-guiding structure of at least one flow manipulation section comprises at least one obstacle for a spinning mass flowing through said flow manipulation section to flow over or under, whereby the obstacle preferably extends, in particular perpendicularly, into the flow manipulation section from the floor surface and/or the ceiling surface of the flow manipulation section and reaches to a defined gap on the ceiling surface and/or the floor surface.

If the flow manipulation section is thereby arranged in a horizontal orientation, relative to a functional state of use of the spinning nozzle, the obstruction to flow over or under preferably extends vertically.

Such an obstacle for flow over or under same can for example be formed by a cylindrical casing extending into the flow manipulation section from the floor surface and/or ceiling surface of the flow manipulation section or a corresponding cylindrical casing section, in particular a circular cylindrical casing-shaped section.

Flowing over and/or flowing under of an obstacle as described above can achieve a particularly simple (further) homogenizing of the spinning mass flow, in particular a defined spinning mass flow can be set. In conjunction with an associated suitable geometry to the outlet port, in particular a suitably defined outlet port gap width, a desired layer thickness of a spinning mass to be extruded from the respective outlet port can consequently be set.

In a further advantageous embodiment of a spinning nozzle according to the invention, the flow-guiding structure of at least one flow manipulation section comprises a plate-shaped body structured by means of microstructure technology, in particular a plate structured by microstructure technology, or is formed by a plate structured by microstructure technology.

Preferably, the structured plate-shaped body and/or the structured plate thereby comprises a wafer or is made of one or more wafers.

Particularly preferentially, the entire flow manipulation section is formed by a plate-shaped body structured by means of microstructure technology and/or by a plate structured by microstructure technology, whereby preferably all the flow manipulation sections are in each case formed by a corresponding body and/or a corresponding plate.

Hollow fiber capillary membranes, in particular ultra-fine hollow fiber capillary membranes with a homogeneous layer structure to the individual layers and a wall thickness in each case of less than 100 nm, in particular approximately 50 nm, can be produced by an inventive spinning nozzle manufactured in this way.

The producing of structured, plate-shaped bodies by means of microstructure technology, in particular the producing of structured plates by means of microstructure technology, is in principle known from the prior art. Further details on how structured, plate-shaped bodies and/or structured plates which are suitable for use in a spinning nozzle according to the invention can be produced can be learned from EP 2 112 556 A1, to which explicit reference is hereby made in this context.

An inventive spinning nozzle is particularly suited to producing dialysis membranes or hollow fiber membranes for use in gas exchangers in conjunction with extracorporeal membrane oxygenation as well as for hollow fiber membranes for separating blood plasma from other blood components, particularly for producing such hollow fiber membranes designed as capillary membranes having diameters of less than 500 nm and a total wall thickness of less than 100 nm, particularly wall thicknesses in the range of approximately 50 nm.

In a further advantageous embodiment of a spinning nozzle according to the invention, the spinning nozzle comprises at least two plates structured by means of microstructure technology, whereby the plates are in a parallel arrangement one above the other and are at least partially bonded together by tempering. This can produce a particularly stable spinning nozzle which can in particular absorb both tensile as well as compressive forces. An "expanding" of the flow manipulation section, in particular a raising of the upper plate from the lower plate due to the spinning mass flow, disadvantageous to a uniform spinning mass flow, can thus be prevented.

An apparatus according to the invention for extruding a plurality of hollow fibers or hollow fiber membranes from one or more spinning masses, wherein the apparatus com-prises a spinning nozzle for each hollow fiber or hollow fiber membrane to be extruded, com-prises at least one spinning nozzle configured in accordance with the invention, whereby preferably all of the spinning nozzles are configured in accordance with the invention.

A method according to the invention for extruding a hollow fiber or hollow fiber membrane from one or more spinning masses by means of a spinning nozzle is characterized by the steps:

Providing a spinning nozzle configured according to the invention or an inventively configured apparatus, Providing one or more spinning masses and, if applicable, one or more reinforcing agents and/or precipitating agents, Feeding the spinning masses, and reinforcing agent and/or precipitating agent as applicable, to the provided spinning nozzle or to the provided apparatus, Introducing the spinning masses, and reinforcing agent and/or precipitating agent as applicable, into the provided spinning nozzle or the provided apparatus via the associated inlet ports, and Extruding the hollow fiber or the hollow fiber membrane by means of the provided spinning nozzle or the apparatus as provided.

If applicable, further steps for post-processing of the extruded hollow fiber or extruded hollow fiber membrane can be performed such as, for example, introducing the extruded hollow fiber or extruded hollow fiber membrane into a precipitation bath or the like.

A plurality of spinning nozzles or a corresponding apparatus comprising a plurality of spinning nozzles according to the invention can simultaneously be used for simultaneously extruding multiple hollow fibers or multiple hollow fiber membranes.

An inventive filter, in particular a dialyzer, a plasma exchange filter or a filter for extracorporeal membrane oxygenation is produced by means of an inventive spinning nozzle, by means of an inventive apparatus, or by means of an inventive method.

These and further features are apparent from the claims and from the description as well as from the figures, wherein the respective individual features can each be realized in an embodiment of the invention on their own or as a plurality in the form of subcombinations, provided same is technically expedient.

BRIEF DESCRIPTION OF THE DRAWINGS

The invention will be described in greater detail in the following on the basis of non-limiting example embodiments as depicted schematically in the figures, whereby unless otherwise described or contextually indicated otherwise, components having the same function have the same reference numerals. The figures show, to some extent schematized.

DETAILED DESCRIPTION

Figure 1:
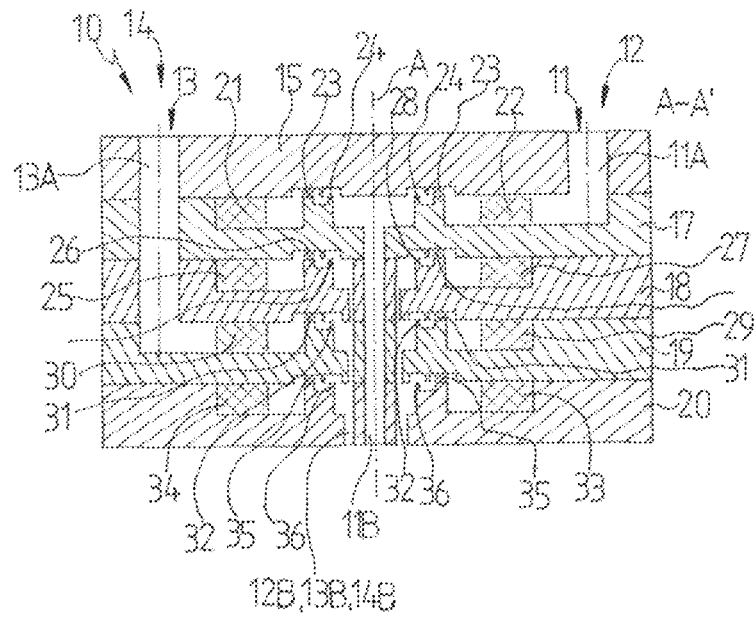
FIG. 1 a first example embodiment of a spinning nozzle according to the invention in a schematic cross-sectional diagram along the A-A' sectional plane, FIG. 2 a second example embodiment of a spinning nozzle according to the invention in a schematic cross-sectional diagram, FIG. 3 an enlarged detail from the FIG. 1 sectional view in the area of the obstructing element and the vertical obstacle in an oblique view of the sectional plane with symbolized spinning mass flow, FIG. 4 the inventive spinning nozzle from FIG. 1 in a perspective representation, FIG. 5 a schematic diagram of a first example embodiment of a configuration of a flow manipulation section of the structured plate produced by microstructure technology of the inventive spinning nozzle from FIG. 1 for influencing the flow of the first spinning mass, FIG. 6 a schematic diagram of a second example embodiment of a a configuration of a flow manipulation section of a structured plate produced by microstructure technology for an inventive spinning nozzle for influencing the flow of the first spinning mass, and FIG. 7 a schematic diagram of a mass flow divider as per a curly bracket.

FIG. 1 shows a schematic sectional view of the structure of a first example embodiment of a spinning nozzle 10 according to the invention which is formed of a microstructured cover plate 15 of four plates 17, 18, 19 and 20 structured by means of microstructure technology arranged thereunder, each produced from silicon wafers. In another configuration of an inventive spinning nozzle, a base plate can be provided underneath plate 20. A further support plate can also be provided above the cover plate 15.

Figure 4:
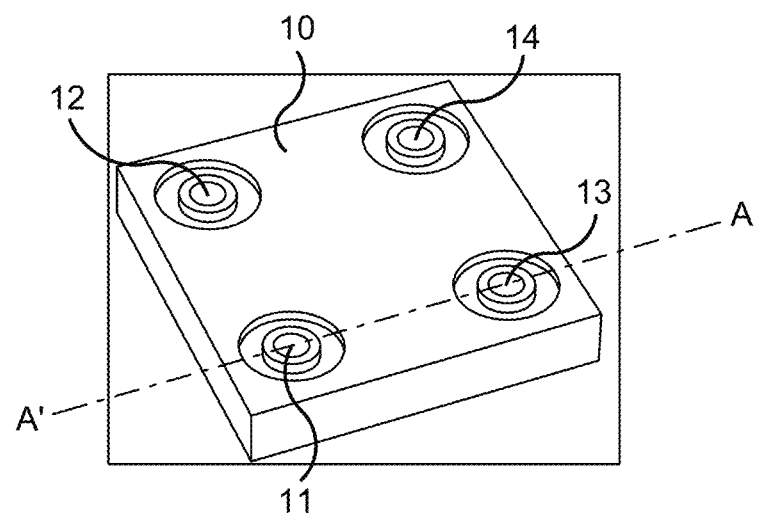

The inventive spinning nozzle 10 is thereby designed for extruding a hollow fiber capillary membrane from three spinning mass layers in the wet-into-wet spinning process, whereby the spinning nozzle comprises a total of four inlet ports 11, 12, 13 and 14 (see FIG. 4) arranged on an upper side of the spinning nozzle 10 relative to a functional state of use of the spinning nozzle 10.

Inlet ports 12, 13 and 14 are thereby provided for the feed of a respective spinning mass while inlet port 11 is provided for the feed of a precipitating agent for curing the hollow fiber membrane exiting from the nozzle.

The spinning nozzle furthermore comprises a respective outlet section 12B, 13B and 14B for each spinning mass to be extruded, each with an outlet port, which is not described in greater detail here, at the end of the respective outlet section 12B, 13B and 14B on an underside of the spinning nozzle 10, whereby the outlet sections 12B, 13B and 14B are gradually merged ahead of the outlet out of the spinning nozzle 10, as well as an outlet section 11B having an outlet port for the precipitating agent likewise arranged on the underside of the spinning nozzle 10.

The inlet ports 11, 12, 13 and 14 are thereby each connected to the respective outlet port by a respective spinning mass flow channel, or a precipitating agent mass flow channel respectively, wherein the outlet ports are arranged concentrically to a common nozzle outlet axis A, along which the individual spinning masses and the precipitating agent can exit out of the spinning nozzle 10.

The precipitating agent mass flow channel thereby comprises, as do all of the respective spinning mass flow channels, a feeding section 11A, whereby only feeding section 13A connected to spinning mass inlet port 13 is visible in FIG. 1.

In order to produce a particularly uniformly formed hollow fiber capillary membrane, in particular with a particularly uniform wall thickness to the individual spinning mass layers circumferentially as well as a particularly uniform wall thickness over their length, as well as a hollow fiber membrane in which the individual membrane layers exhibit virtually no concentricity errors, a respective flow manipulation section, not described in greater detail here, is provided in each mass flow channel between the associated feeding section and the respective outlet section 11B, 12B, 13B, 14B which is in each case formed by the associated, microstructured plate 17, 18, 19 or 20 respectively.

The flow manipulation section for influencing the precipitating agent mass flow is thereby formed by microstructured plate 17, the flow manipulation section for influencing the first spinning mass introducible into the spinning nozzle via inlet port 12 by microstructured plate 18, the flow manipulation section for influencing the spinning mass flow of the second spinning mass introducible through inlet port 13 by microstructured plate 19, and the flow manipulation section for the third spinning mass introducible into the spinning nozzle 14 via inlet port 14 is correspondingly formed by microstructured plate 20.

All the flow manipulation sections of the inventive spinning nozzle 10 depicted in FIG. 1 are thereby designed such that a flow-guiding structure influences a mass flowing through the respective flow channel such that at least a portion of the mass flowing through the flow channel flows along at least two different flow paths, wherein all the flow paths from the inlet in the respective flow manipulation section to the associated outlet port for the respective mass have the same path length, wherein the respective outlet ports for all the masses are disposed on the underside of the spinning nozzle 10 in the inventive spinning nozzle 10 depicted as an example in FIG. 1.

For the inventive influencing of the respective mass flows as described above, all the microstructured plates 17, 18, 19 and 20 of the inventive spinning nozzle 10 depicted in FIG. 1 comprise a plurality of flow guidance elements 21, 22, 25, 27, 29, 30, 33 and 34, only indicated schematically in FIG. 1, which are in particular configured as mass flow dividers in this embodiment and each able to halve an incoming mass flow.

Each flow manipulation section, or each microstructured plate 17, 18, 19, 20 respectively, furthermore exhibits an obstructing element 23, 26, 31 or 35 respectively, which comprises a plurality of flow openings 70, not described in greater detail here (see FIG. 3), uniformly arranged within the obstructing element 23, 26, 31 or 35, through which the respective mass flow must flow in order to reach the associated outlet port.

All the flow manipulation sections are thereby formed by a volume limited by a flat floor surface, a flat ceiling surface as well as side surfaces oriented perpendicular thereto, wherein all of the flow guidance elements 21, 22, 25, 27, 29, 30, 33 and 34 in each case extend perpendicularly from the respectively associated floor surface to the associated ceiling surface of the respective flow manipulation section in this example embodiment.

The obstructing elements 23, 26, 31 and 35 are thereby formed in each case by a circular cylinder casing and likewise extend perpendicularly from the respectively associated floor surface of the respective flow manipulation section to the respectively associated ceiling surface, wherein the obstructing elements 23, 26, 31 and 35 in this case are of multi-part configuration and comprise a projection allocated to one of the respective upper plates forming the ceiling surface of the associated flow manipulation section and a respective projection allocated to the lower plate forming the floor surface of the associated flow manipulation section. In order to prevent an "expanding" of the flow manipulation section, in particular a raising of the upper plate from the lower plate, due to the spinning mass flow, the two projections are respectively bonded together by tempering.

Before the respective mass flow reaches the respectively associated outlet section 11B, 12B, 13B or 14B after exiting the flow openings of the obstructing elements 23, 26, 31 and 35, the mass flow must in each case flow over a vertical obstacle 24, 28, 32 or respectively 36 extending in this example embodiment from the floor surface to a gap at the respective ceiling surface in order to then ultimately be able to flow through the respectively associated outlet section to the associated outlet port on the underside of the spinning nozzle 10.

Figure 3:
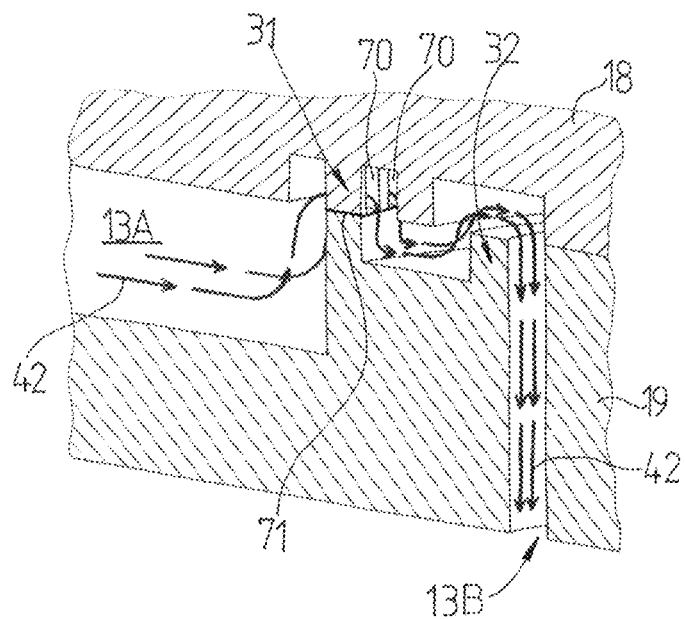

This is particularly clear from FIG. 3 which shows an enlarged detail of the sectional view from FIG. 1 in the area of the obstructing element 31 and the vertical obstacle 32 in an oblique view of the sectional plane with the spinning mass flow 42 for the second spinning mass symbolized by arrows having a bonding area 71 in the center of obstructing element 31 below the flow openings 70 between the upper plate 18 and the lower plate 19.

Figure 2:
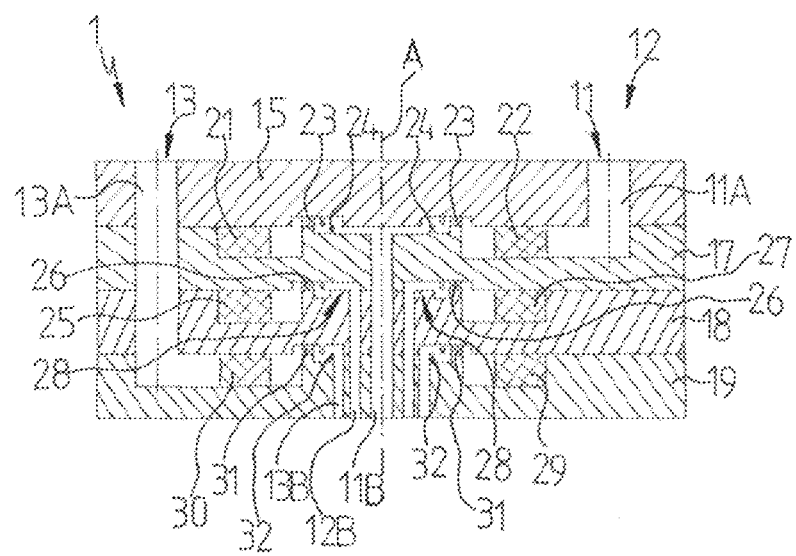

FIG. 2 shows a second example embodiment of a spinning nozzle 1 according to the invention in a schematic cross-sectional diagram, whereby in addition to the cover plate 15, this spinning nozzle only comprises three microstructured plates 17, 18 and 19 and is thus designed to only produce a hollow fiber membrane from two spinning masses. As in the example embodiment of an inventive spinning nozzle 10 described above, the uppermost plate 17 thereby likewise serves to influence the flow of the precipitating agent mass flow, and plates 18 and 19 to respectively influence the flow of a spinning mass flow.

A further difference from the spinning nozzle 10 of FIG. 1 is that in the spinning nozzle 1 depicted in FIG. 2, the outlet sections 12B and 13B for the individual spinning masses do not merge within the nozzle but rather each run separately to the nozzle outlet. In other words, this spinning nozzle 1 does not allow for wet-into-wet merging of the individual spinning masses but is instead designed for so-called dry merge in which the individual spinning masses are not brought into contact with each other until after exiting from the spinning nozzle.

Figure 5:
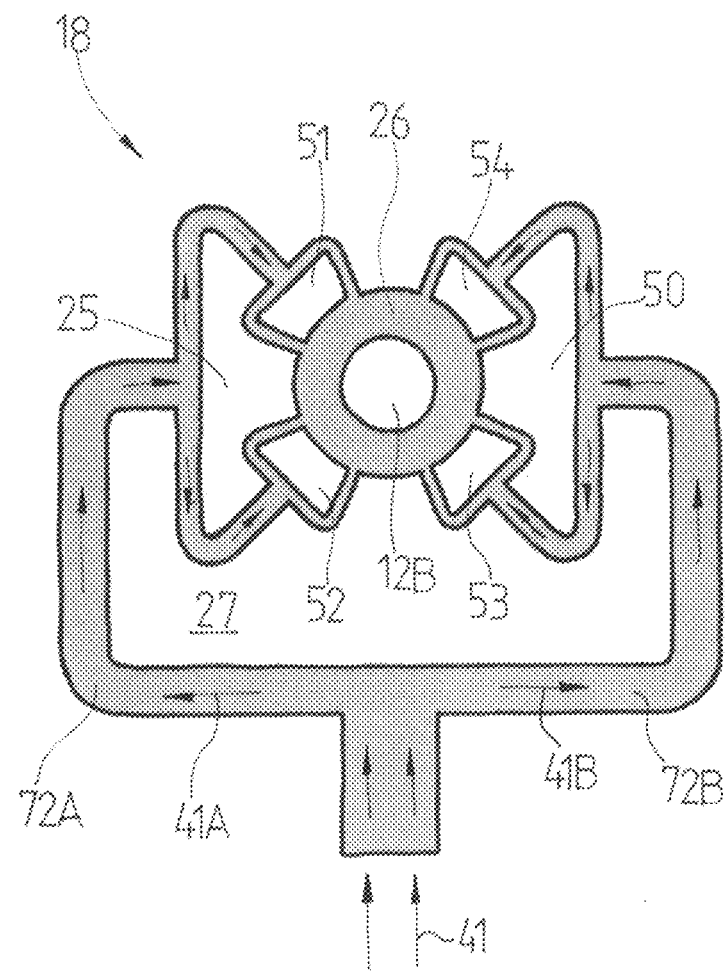

FIG. 5 shows a schematic diagram of a first example embodiment of a configuration of a flow manipulation section for influencing the first spinning mass flow for the structured plate 18 of the inventive spinning nozzle from FIG. 1 produced by microstructure technology which forms the flow manipulation section for the first spinning mass introducible into the spinning nozzle 10 via inlet port 12, wherein the spinning mass feed ensues at the lower middle relative to the depiction in FIG. 5. That is to say that the inlet of the flow manipulation section, which is formed by microstructured plate 18, is disposed at the lower middle, here in particular in the ceiling surface of the plate 18, which is in particular formed by an underside of the overlying plate 17.

The flow manipulation section comprises a plurality of flow guidance elements 25, 27, 51, 52, 53 and 54 respectively symmetrical to a first symmetrical plane extending perpendicular to the floor surface of the flow manipulation section which are at least partly configured as mass flow dividers in each case and in each case exhibit a straight leading edge as a flow-directing contour which acts to divide, in particular bisect, the flow into two halves.

In some specific applications it can be advantageous when instead of a straight flow-directing contour in an inventive spinning nozzle; i.e. instead of a straight leading edge, at least one mass flow divider exhibits a flow-directing contour which is formed similar to or as per a curly bracket, wherein preferably the tip at the bracket's center is oriented toward the direction of flow of the spinning mass flow; i.e. faces the inflowing mass.

The flow guidance elements 25, 27, 51, 52, 53 and 54 of the flow manipulation section depicted schematically in FIG. 5 thereby form a cascade, in the present case a three-stage cascade, by means of which the supplied spinning mass flow 41 can be divided gradually.

The first stage of the cascade thereby only comprises just one flow guidance element 27 in the form of a mass flow divider 27 which divides the spinning mass flow 41 of the first spinning mass 41 into a first portion 41A, in particular a first half 41A, and a second portion 41B, in particular a second half 41B, so that the spinning mass 41 is guided toward the outlet section 12B along two different flow paths 72A and 72B.

The second stage of the cascade comprises two mass flow dividers 25 and 50 which in turn divide the incoming spinning mass 41A/41B such that the spinning mass 41 is then guided toward the outlet section 12B along four flow paths, whereby the length of the flow-directing contour of the two mass flow dividers 25 and 50 in this example embodiment is in each case a length which is ¼ that of the flow-directing contour of the mass flow divider 27 of the previous, here the first, cascade stage, and wherein the two mass flow dividers 25 and 50 of the second stage of the cascade are each arranged with a respective offset orientation of 90° to the mass flow divider 27 of the first stage of the cascade.

The third stage of the cascade is formed by a total of four mass flow dividers 51, 52, 53, and 54 which are each arranged at a respective 45° offset to the two mass flow dividers 25 and 50 of the second cascade stage and their flow contour lengths likewise amount in each case to exactly ¼ the length of the flow contour of the mass flow dividers 25 and 50 of the previous second cascade stage.

The division of the spinning mass flow 41 thereby continues with each cascade stage so that the spinning mass 41 is as a result led toward outlet section 12B along at least 8 flow paths in the case of a flow manipulation section designed in accordance with FIG. 5.

An obstructing element 26 comprising flow openings not visibly depicted here (see FIG. 3) is moreover further provided in the direction of flow, through which the respective mass flow must pass in order to reach the respective outlet section 12B and farther on to the associated outlet of the spinning nozzle. In addition to further homogenizing the mass flow, an aligning of the mass flow and a particularly uniform mass feed can also be achieved by means of such an obstructing element 26. The number of flow paths can be even further increased by corresponding flow openings in the obstructing element 26.

Although not visibly depicted in FIG. 5, the flow manipulation section further comprises a vertical obstacle (see FIG. 3, reference numeral 32) downstream of obstructing element 26.

By means of a previously described inventively configured flow manipulation section, a mass flow can be guided from the inlet of the flow manipulation section to the outlet of the flow manipulation section or the associated outlet port respectively along a plurality of different flow paths 72A, 72B such that all portions of the mass flow, or all of the flow paths along which the mass flow is guided respectively, exhibit the same path length.

Figure 6:
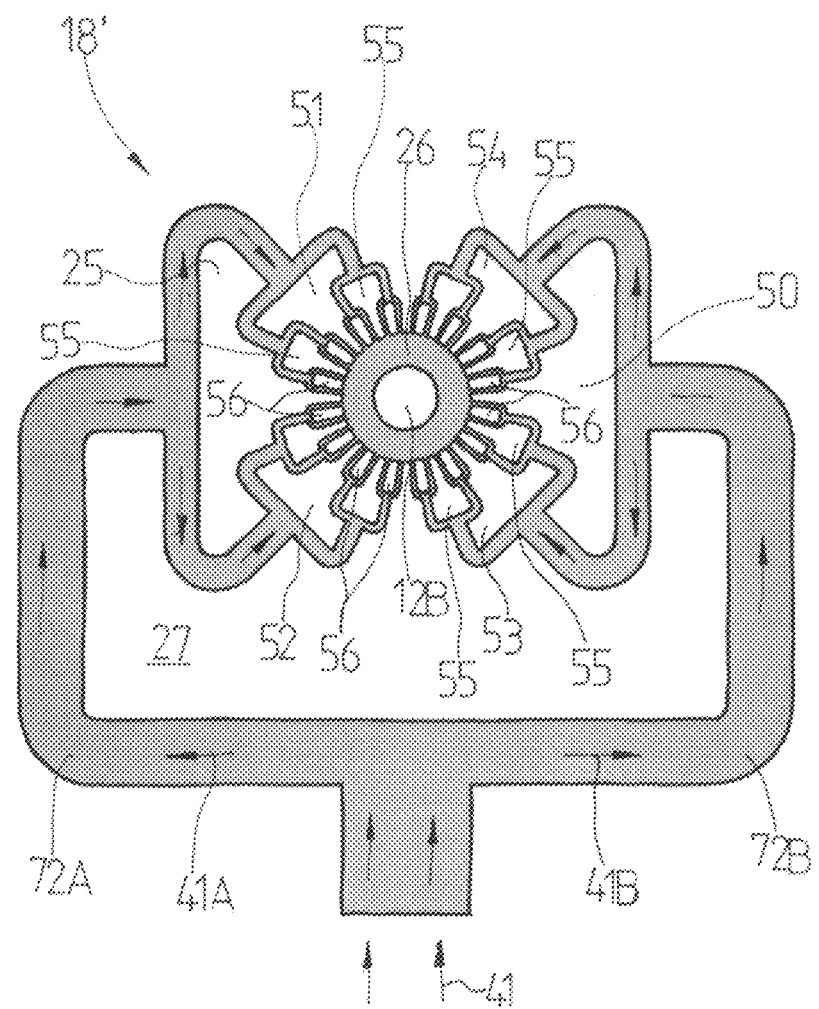

FIG. 6 shows a schematic diagram of a second example embodiment of a flow manipulation section configuration for influencing the flow of the first spinning mass of a structured plate 18' produced by microstructure technology for an inventive spinning nozzle.

Compared to the flow manipulation section from FIG. 5, the flow manipulation section depicted schematically in FIG. 6 comprises further flow guidance elements 55 and 56 which form a five-stage cascade with the flow guidance elements 25, 27, 51, 52, 53 and 54 by means of which the supplied spinning mass flow 41 can likewise be divided gradually. The spinning mass 41 can as a result thus be guided toward the outlet section 12B along at least 32 flow paths.

The first three stages of the cascade are thereby configured like the flow manipulation section described on the basis of FIG. 5.

The fourth stage of the cascade is formed by a total of eight flow guidance elements in the form of mass flow dividers 55, each arranged at a 22.5° offset to the mass flow dividers 51, 52, 53 and 54 of the previous third cascade stage and the length of their flow-directing contours likewise amounting to exactly ¼ the length of the flow-directing contours of the mass flow dividers of the previous cascade stage.

The fifth cascade stage comprises flow guidance elements 56 likewise exhibiting flow-directing contours designed as mass flow dividers, whereby a total of 16 flow guidance elements 56 are provided in the fifth cascade stage, in each case distributed circumferentially uniformly on a common radius concentric to the associated outlet section 12B and likewise in a respectively uniform offset arrangement to the mass flow dividers 55 of the fourth cascade stage.

In contrast to the flow guidance elements of the previous cascade stage, the flow guidance elements 56 of the fifth cascade stage exhibit an elongated section extending radially inwardly on a far side from the leading edge; i.e. its rear.

It has proven particularly advantageous in some specific applications for the flow guidance elements of the innermost cascade stage to comprise at least some flow-directing contours, in particular some flow-directing contours formed as flow guidance elements 56 of the fifth cascade stage in a five-stage cascade which are similar to or as per a curly bracket and in each case with no symmetrically formed and symmetrically arranged geometry on the far side of the flow-directing contour but rather an asymmetrically formed guide vane section.

Preferably, each radially inwardly pointing end of the individual guide vanes are thereby concentrically arranged on a circular path relative the outlet section 12B and formed such that a mass flow exiting inwardly between the guide vane sections exits at least one guide vane section tangentially with respect to the associated outlet section 12B.

As clearly identifiable from FIGS. 5 and 6, the spinning mass flow introduced into the flow manipulation section is thereby divided into a plurality of spinning mass flow portions in the flow manipulation section of the microstructured plate 18 and diverted multiple times. The path lengths of the individual flow paths, in particular over the respective flow guidance elements, is thereby specifically influenced and/or changed such that the same path length is inventively set for all the flow paths, same in particular being achieved by means of the geometric configuration and arrangement to the individual flow guidance elements.

While also serving to influence the path length of the individual flow paths, the obstructing element 26 primarily serves to further homogenize and align the mass flow.

By means of the embodiments of a flow manipulation section for an inventive spinning nozzle depicted in FIGS. 5 and 6, a spinning nozzle with virtually no dead zones configured in the spinning mass flow channel can in particular be provided.

A particularly uniform and constant spinning mass feed to the associated outlet section can be achieved, whereby the respective spinning mass layer can be produced with a very uniform wall thickness circumferentially as well as over the length.

Figure 7:
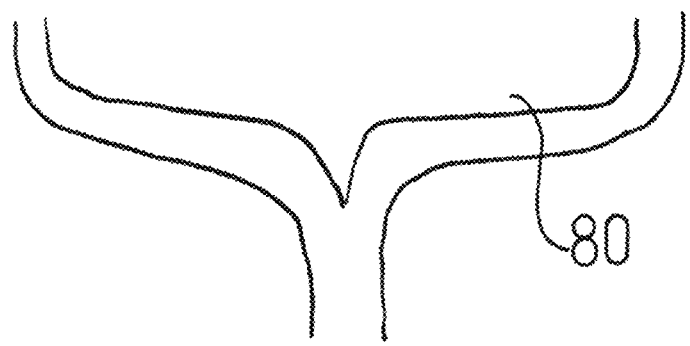

FIG. 7 depicts a mass flow divider 80 as per a curly bracket. Such embodiments can be implemented particularly aerodynamically.

A particularly advantageously designed inventive spinning nozzle 10 in accordance with FIG. 1 having a flow manipulation section according to FIG. 6 exhibits the advantageous dimensions indicated in table 1 for the individual microstructured plates 17, 18, 19 and 20 at the allocation as specified below:

AStrömE area of the flow guidance elements of the respective plate
AStauE area of the obstructing elements of the respective plate
AAustritt cross-sectional area of the outlet section out of the respective plate
Di inner diameter of the respective outlet section
D outer diameter of the respective outlet section
h1 height of the respective mass flow channel in the area of flow guidance elements 56
h2 height of the respective flow openings
l2 length of the respective flow openings
l3 length of the respective outlet section
V0 flow rate upon exiting the flow guidance element 56 sections of the fifth cascade stage
V1 flow rate upon entering into the obstructing element
V2 flow rate upon entering into the outlet section
S1 gap width between two flow guidance elements 56 at the gap outlet
S2 gap width of flow openings 70
S3 gap width of the respective outlet port/respective outlet section

TABLE 1

Advantageous dimensions for an inventive spinning nozzle 10

|  | Plate 17 | Plate 18 | Plate 19 | Plate 20 |
| --- | --- | --- | --- | --- |
| V0 | 710 mm/s | 7.5 mm/s | 7.5 mm/s | 83 mm/s |
| V1 | 730 mm/s | 23.3 mm/s | 15 mm/s | 223 mm/s |
| V2 | 1270 mm/s | 32 mm/s | 15 mm/s | 223 mm/s |
| S1 | 44 μm | 44 μm | 44 μm | 44 μm |
| S2 | 14 μm | 10 μm | 14 μm | 14 μm |
| S3 | — | 10 μm | 20 μm | 50 μm |
| $D_i$ | — | 200 μm | 200 μm | 200 μm |
| D | 100 μm | 210 μm | 210 μm | 250 μm |
| h1 | 20 μm | 40 μm | 40 μm | 150 μm |
| h2 | 14 μm | 10 μm | 14 μm | 40 μm |
| l2 | — | 50 μm | 50 μm | 50 μm |
| l3 | 640 μm | 80 μm | 80 μm | 150 μm |
| $A_{StrömE}$ | 880 μm² × 16 | 1760 μm² × 16 | 1760 μm² × 16 | 6600 μm² × 16 |
| $A_{StauE}$ | 196 μm² × 70 | 100 μm² × 90 | 196 μm² × 70 | 560 μm² × 70 |
| $A_{Austritt}$ | 7854 μm² | 6597 μm² | 13823 μm² | 39270 μm² |

The indicated values thereby refer to a spinning speed of 300 mm/s at a mass flow feed of 8.75 mg/s for the spinning mass of the outermost hollow fiber layer, a mass flow feed of 0.21 mg/s for the mass flow of the middle spinning mass layer as well as a mass flow feed for the mass flow of the innermost spinning mass layer of 0.21 mg/s and a mass flow feed of approximately 10 mg/s for the precipitating agent.

It is obvious that a plurality of modifications, particularly of a structural nature, is possible without departing from the content of the claims.

LIST OF REFERENCE NUMERALS

1, 10 inventive spinning nozzle
11 inlet port for precipitating agent feed
11A feeding section of the precipitating agent mass flow channel
11B outlet section of precipitating agent mass flow channel
12 inlet port for a first spinning mass feed
12B outlet section of first spinning mass flow channel
13 inlet port for a second spinning mass feed
13A feeding section of the spinning mass flow channel of the second spinning mass
13B outlet section of second spinning mass flow channel
14 inlet port for a third spinning mass feed
14B outlet section of the third spinning mass flow channel
15 cover plate
17 microstructured plate with a flow manipulation section for influencing the flow of a precipitating agent mass flow
18, 18' microstructured plate with a flow manipulation section for influencing the flow of the first spinning mass
19 microstructured plate with a flow manipulation section for influencing the flow of a second spinning mass
20 microstructured plate with a flow manipulation section for influencing the flow of a third spinning mass
21 flow guidance element
22 flow guidance element
23 obstructing element 24 vertical obstacle
25 flow guidance element; mass flow divider of second cascade stage
26 obstructing element
27 flow guidance element; mass flow divider of second cascade stage
28 vertical obstacle
29 flow guidance element
30 flow guidance element
31 obstructing element
32 vertical obstacle
33 flow guidance element
34 flow guidance element
35 obstructing element
36 vertical obstacle
41 spinning mass flow of first spinning mass
41A first portion of the spinning mass flow of the first spinning mass
41A second portion of the spinning mass flow of the first spinning mass
42 spinning mass flow of second spinning mass
50 flow guidance element; mass flow divider of second cascade stage
51 flow guidance element; mass flow divider of third cascade stage
52 flow guidance element; mass flow divider of third cascade stage
53 flow guidance element; mass flow divider of third cascade stage
54 flow guidance element; mass flow divider of third cascade stage
55 flow guidance element; mass flow divider of fourth cascade stage
56 flow guidance element of fifth cascade stage
70 flow opening
71 bonding area
72A first flow path
72B second flow path
80 mass flow divider as per a curly bracket
A nozzle outlet axis

The invention claimed is:

1. A spinning nozzle for extrusion of a hollow fiber membrane from a plurality of spinning masses, wherein
the spinning nozzle has a plurality of inlet ports, including an inlet port for each respective spinning mass to be extruded, each inlet port being configured for introducing the respective spinning mass into the spinning nozzle,
the spinning nozzle has a plurality of nozzle outlet ports, each nozzle outlet port being configured for an exit of one or more of the plurality of spinning masses out of the spinning nozzle along a respective outlet axis,
the spinning nozzle has a plurality of spinning mass flow channels, each spinning mass flow channel having a channel inlet port and a channel outlet port and being configured for guiding a respective one of the plurality of spinning masses from a respective one of the channel inlet ports to a respective one of the channel outlet ports,
at least one of the spinning mass flow channels comprises a first flow manipulation section having a single inlet and a plurality of flow openings through which the respective one of the plurality of spinning masses must pass in order to reach the respective channel outlet port, the first flow manipulation section comprising a flow-guiding structure for guiding the respective spinning mass through the respective spinning mass flow channel between the single inlet and the plurality of flow openings of the first flow manipulation section,
the flow-guiding structure is configured to guide the respective spinning mass such that at least a portion of the respective spinning mass flows through the first flow manipulation section along different flow paths, wherein the flow-guiding structure comprises a plurality of cascaded mass flow dividers, dividing the respective spinning mass into the different flow paths, and each of the different flow paths begins at the single inlet and ends at the respective channel outlet port,
each of the different flow paths running through the first flow manipulation section has a respective path length between the single inlet and the respective channel outlet port, and
all of the respective path lengths are the same.

2. The spinning nozzle according to claim 1, wherein at least one of the plurality of inlet ports is an agent inlet port for introducing a reinforcing agent and/or a precipitating agent into the spinning nozzle, at least one of the plurality of nozzle outlet ports is an agent outlet port for the reinforcing agent and/or precipitating agent to exit out of the spinning nozzle along the respective outlet axis, at least one of the plurality of spinning mass flow channels is a feed channel for conducting the reinforcing agent and/or precipitating agent from the agent inlet port to the agent outlet port, the plurality of channel outlet ports includes an innermost channel outlet port, the agent outlet port is disposed radially inside the innermost channel outlet port, and the agent outlet port is configured concentrically with respect to the innermost channel outlet port.

3. The spinning nozzle according to claim 1, wherein each of the plurality of the spinning mass flow channels comprises a respective flow manipulation section, and the first flow manipulation section is arranged in a perpendicular orientation with respect to the respective outlet axis.

4. The spinning nozzle according to claim 1, wherein all of the inlet ports of the plurality of inlet ports are arranged on the upper side of the spinning nozzle with respect to a functional state of use of the spinning nozzle.

5. The spinning nozzle according to claim 1, wherein the single inlet of the first flow manipulation section is arranged eccentrically with respect to the respective outlet axis and arranged radially outwardly with respect to a respective one of the plurality of nozzle outlet ports, relative to the respective outlet axis.

6. The spinning nozzle according to claim 1, wherein the each of the plurality of flow openings of the first flow manipulation section is arranged concentrically to the respective outlet axis, each of the plurality of flow openings of the first flow manipulation section is of a design that is congruent to a design of a respective one of the plurality of nozzle outlet ports, and each of the plurality of flow openings of the first flow manipulation section is arranged parallel to the respective one of the plurality of nozzle outlet ports.

7. The spinning nozzle according to claim 1, wherein the flow-guiding structure comprises one or more flow guidance elements and/or one or more obstructing elements.

8. The spinning nozzle according to claim 7, wherein at least one of the one or more flow guidance elements is formed by a projection having a wall extending from a floor surface to a ceiling surface of the first flow manipulation section, and the wall at least partially forms a flow guide surface and has a defined flow-directing contour.

9. The spinning nozzle according to claim 7, wherein at least one of the one or more flow guidance elements comprises a flow-directing contour that is symmetrical to a first symmetrical plane, and the first symmetrical plane extends perpendicularly with respect to a flow of the respective one of the plurality of spinning masses during operation.

10. The spinning nozzle according to claim 7, wherein at least one of the one or more flow guidance elements comprises a flow-directing contour having a front face cross-sectional shape in the form of a curly bracket.

11. The spinning nozzle according to claim 7, wherein the plurality of cascaded mass flow dividers comprises the one or more flow guidance elements, arranged in a cascade.

12. The spinning nozzle according to claim 11, wherein the one or more flow guidance elements comprises at least three flow guidance elements arranged in the cascade, the cascade has a single one of the at least three flow guidance elements in a first stage of the cascade, the cascade has two of the at least three flow guidance elements in a second stage of the cascade, and the flow guidance elements of the second stage are arranged at an offset orientation of approximate+/−90° relative to the single flow guidance element in the first stage.

13. The spinning nozzle according to claim 12, wherein the at least three flow guidance elements arranged in the cascade include 2 (n−1) flow guidance elements that are, in each case, provided in an nth stage for n>=2, and the 2 (n−1) flow guidance elements are arranged offset by a respective 180°/2 (n−1) angle with respect to the flow guidance elements of an (n−1)th stage.

14. The spinning nozzle according to claim 11, wherein the one or more flow guidance elements comprises at least three flow guidance elements arranged in the cascade, one of the at least three flow guidance elements is of an nth stage of the cascade, one of the at least three flow guidance elements is of an (n−1)th stage of the cascade, and a length of a flow-directing contour of the flow guidance element of the nth stage of the cascade amounts to ¼ a length of a flow-directing contour of the flow guidance element of the (n−1)th stage.

15. The spinning nozzle according to claim 7, wherein at least one of the one or more flow guidance elements comprises a guide vane, and the guide vane at least partially conducts a flow of the respective one of the plurality of spinning masses toward a respective one of the plurality of nozzle outlet ports during operation.

16. The spinning nozzle according to claim 15, wherein the at least one flow guidance element that comprises a guide vane comprises a plurality of guide vanes arranged concentrically with respect to the respective one of the plurality of nozzle outlet ports and at an even circumferential distribution, each guide vane has an end, the ends of the guide vanes lie radially inwardly with respect to each of the plurality of flow openings of the first flow manipulation section and are arranged on a circular path of constant radius.

17. The spinning nozzle according to claim 15, wherein the at least one flow guidance element that comprises a guide vane is a flow guidance element of a highest cascade stage, and the guide vane is of one-piece and/or integral design with the flow guidance element of the highest cascade stage.

18. The spinning nozzle according to claim 7, wherein the flow-guiding structure comprises the one or more obstructing elements, and at least one of the one or more obstructing elements is formed by a wall extending from a floor to a ceiling of the first flow manipulation section.

19. The spinning nozzle according to claim 7, wherein the flow-guiding structure comprises the one or more obstructing elements, and at least one of the one or more obstructing elements is formed by a circular cylindrical casing that is arranged concentrically with respect to: the plurality of flow openings of the first flow manipulation section; a respective one of the plurality of nozzle outlet ports; and/or the respective outlet axis.

20. The spinning nozzle according to claim 1, wherein: the flow-guiding structure comprises at least one obstacle that the respective spinning mass flows over or under when flowing through the first flow manipulation section, in operation; the at least one obstacle extends into the first flow manipulation section from a floor and/or a ceiling of the first flow manipulation section; and the at least one obstacle reaches into a defined gap on the ceiling and/or on the floor.

21. The spinning nozzle according to claim 1, wherein the flow-guiding structure comprises a plate-shaped body structured by means of microstructure technology.

22. The spinning nozzle according to claim 1, wherein the spinning nozzle comprises at least two plates structured by means of microstructure technology, the at least two plates are arranged parallel to one another and one above the other, and the at least two plates are at least partially bonded together by tempering.

23. An apparatus comprising the spinning nozzle of claim 1, and a supply of masses to be spun to form the plurality of spinning masses, wherein the apparatus is configured for extruding a plurality of hollow fibers or hollow fiber membranes from the plurality of spinning masses.

24. A method for extruding a hollow fiber or hollow fiber membrane by means of the spinning nozzle of claim 1, comprising the steps of:
providing the spinning nozzle,
providing the plurality of spinning masses,
feeding the plurality of spinning masses into the spinning nozzle, and
extruding the hollow fiber or the hollow fiber membrane from the spinning nozzle.

* * * * *